(12) United States Patent
Ma et al.

(10) Patent No.: US 11,879,884 B1
(45) Date of Patent: Jan. 23, 2024

(54) CLASSIFICATION METHOD AND SYSTEM FOR FINE-GRAINED MIXED SEDIMENTARY ROCKS, MEDIUM, AND TERMINAL

(71) Applicant: Chengdu University of Technology, Chengdu (CN)

(72) Inventors: Yiquan Ma, Chengdu (CN); Xiaofeng Liu, Chengdu (CN); Yangbo Lu, Chengdu (CN); Yongchao Lu, Chengdu (CN); Chen Zhang, Chengdu (CN); Xuebin Du, Chengdu (CN); Zhanhong Liu, Chengdu (CN); Wei Wei, Chengdu (CN); Yi Shu, Chengdu (CN); Jingyu Zhang, Chengdu (CN); Ke Zhao, Chengdu (CN); Qinyu Cui, Chengdu (CN); Hao Wang, Chengdu (CN); Xiaojie Fan, Chengdu (CN); Caiguang Zhi, Chengdu (CN); Mengtian Gao, Chengdu (CN); Lingna Shi, Chengdu (CN)

(73) Assignee: Chengdu University of Technology, Chengdu (CN)

(*) Notice: Subject to any disclaimer, the term of this patent is extended or adjusted under 35 U.S.C. 154(b) by 0 days.

(21) Appl. No.: 18/363,686

(22) Filed: Aug. 1, 2023

(30) Foreign Application Priority Data

Aug. 10, 2022 (CN) .......................... 202210955995.1

(51) Int. Cl.
*G01N 33/24* (2006.01)
*G01N 23/2005* (2018.01)
(Continued)

(52) U.S. Cl.
CPC .......... *G01N 33/24* (2013.01); *G01N 1/2813* (2013.01); *G01N 1/38* (2013.01); *G01N 23/2005* (2013.01);
(Continued)

(58) Field of Classification Search
CPC ........ G01N 33/24; G01N 1/2813; G01N 1/38; G01N 23/2005; G01N 2033/243; G06F 18/24317; G06F 18/2431
See application file for complete search history.

(56) References Cited

U.S. PATENT DOCUMENTS 10,502,863 B2 * 12/2019 Mosse ................. G01V 99/005
2021/0032975 A1 * 2/2021 Teotonio Da Silva .. G01V 3/34

FOREIGN PATENT DOCUMENTS

CN 104007484 A 8/2014
CN 106840741 A * 6/2017
(Continued)

OTHER PUBLICATIONS

Xin Jiao "Fine-grained volcanic-hydrothermal sedimentary rocks in Permian Lucaogou Formation, Santanghu Basin, NW China: Implications on hydrocarbon source rocks and accumulation in lacustrine rift basins" Marine and Petroleum Geology, pp. 1-23 (Year: 2020).*
(Continued)

*Primary Examiner* — Michael J Dalbo
*Assistant Examiner* — Kaleria Knox
(74) *Attorney, Agent, or Firm* — Nitin Kaushik

(57) ABSTRACT

The present disclosure discloses a classification method and system for fine-grained mixed sedimentary rocks, a medium and a terminal. Core description and thin section observation are used to accurately identify the sedimentary structure types and their vertical distribution characteristics from the macroscopic and microscopic perspectives, and indicates the mixed sedimentation characteristics of combination of dif- (Continued)

ferent lamina or laminar couplets. The micro-drilling sampling technique is used to sample the samples with different types of sedimentary structures while avoiding diagenetic minerals. X-ray diffraction mineral content analysis and a high-precision carbon-sulfur analyzer are used to obtain the contents of different types of minerals and the total organic carbon contents in each sample, respectively, the basic rock type of each sample was determined using a triangular classification diagram. The name of sedimentary structure and the total organic carbon content are added in order before the name of the basic rock type.

9 Claims, 3 Drawing Sheets

(51) Int. Cl.
  *G01N 1/28* (2006.01)
  *G06F 18/2431* (2023.01)
  *G06F 18/243* (2023.01)
  *G01N 1/38* (2006.01)
(52) U.S. Cl.
  CPC .... *G06F 18/2431* (2023.01); *G06F 18/24317* (2023.01); *G01N 2033/243* (2013.01)

(56) References Cited

FOREIGN PATENT DOCUMENTS

| | | | |
|---|---|---|---|
| CN | 108387413 | A | 8/2018 |
| CN | 108680594 | A | 10/2018 |
| CN | 113307417 | A * | 8/2021 |
| UA | 847142 | C2 * | 9/2008 |

OTHER PUBLICATIONS

Peng Jun "Discussion on classification and naming scheme of fine-grained sedimentary rocks" , pp. 121-132, Feb. 2022.*
Zhang "Characterization of lacustrine mixed fine-grained sedimentary rocks using coupled chemostratigraphic-petrigraphic analysis: A case study from a tight oil reservoir in the Jumusar Sag, Junggar Basin", pp. 453-472 (Year: 2019).*
Title of the Item: Journal of Northeast Petroleum University Publication Date: Apr. 30, 2016 Name of the Author: Fu Hao et al. Article Title: Geochemical characteristics and genetic model of Cambrian dolomite in east Tarim basin pp. 47-58.
Title of the Item: Petroleum Exploration and Development Publication Date: Feb. 28, 2022 Name of the Author: Peng Jun et al. Article Title: Discussion on classification and naming scheme of fine-grained sedimentary rocks pp. 106-115.

* cited by examiner

S101: performing a systematic core description, thin section collection and observation to accurately identify the sedimentary structure types of fine-grained mixed sedimentary rock samples and vertical distribution characteristics of the sedimentary structure types through the combination of macroscopic and microscopic analysis; and performing a systematical sampling of the fine-grained mixed sedimentary rocks with different types of sedimentary structures while avoiding diagenetic minerals, by using micro-drilling S102: analyzing the mineral composition and the total organic carbon (TOC) content in each sample by using X-ray diffraction and a high-precision carbon-sulfur analyzer, to obtain the contents of different types of minerals and the total organic carbon (TOC) content in each sample S103: classifying the fine-grained mixed sedimentary rock types by using the triangular classification diagram based on quartz + feldspar contents, carbonate content, and clay minerals contents, to determine 4 major categories and 18 sub-categories of basic rock types S104: Prefixing the names of the classified basic rock types with the names of sedimentary structures, and marking the total organic carbon (TOC) contents of different samples before the names of sedimentary structures

FIG. 1

CLASSIFICATION METHOD AND SYSTEM FOR FINE-GRAINED MIXED SEDIMENTARY ROCKS, MEDIUM, AND TERMINAL

CROSS-REFERENCE TO RELATED APPLICATIONS

The application claims priority to Chinese patent application No. 2022109559951, filed on Aug. 10, 2022, the entire contents of which are incorporated herein by reference.

TECHNICAL FIELD

The present disclosure belongs to the technical field of classification of fine-grained mixed sedimentary rocks, and particularly relates to a classification method and system for fine-grained mixed sedimentary rocks, a medium, and a terminal.

BACKGROUND

In recent years, with the continuous breakthroughs in the exploration and development of unconventional oil and gas resources worldwide, shale oil and gas resources have become a major field of oil and gas exploration today and in the future.

As the source rocks and reservoirs of shale oil and gas resources, the fine-grained mixed sedimentary rocks are the core research carrier for shale oil and gas exploration and development in continental basins. Shale oil and gas geological theory and exploration practice show that how to correctly classify the fine-grained mixed sedimentary rocks is the core issue to effectively identify the sweet spot of shale oil and gas development, and is also the key to successful shale oil and gas exploration. Obviously, establishing a classification method for fine-grained mixed sedimentary rocks applicable to theoretical research and production practice, and identifying high-quality fine-grained mixed sedimentary rock types are the key technical problems that need to be solved urgently in the present.

Previous researchers have also made some explorations for the classification of continental fine-grained mixed sedimentary rocks. They performed the classification of fine-grained mixed sedimentary rocks mainly based on the plotting mineral compositions in the triangular diagram. Firstly, the obtained mineral contents of the fine-grained mixed sedimentary rocks were put in the triangular diagram with three end-members of quartz+feldspar content, carbonate content, and clay minerals (or volcanogenic debris) content, respectively. Different zones are classified in the triangular diagram, with respective mineral contents of 10%, 25%, 50%, and 75% as boundaries in different end-members. Second, the basic fine-grained mixed sedimentary rock types of these samples are named according to the different zones of the sample points in the triangular diagram, and finally, a comprehensive naming is performed in combination with the sedimentary structures (laminated, layered, massive) of the samples.

Problems and defects present in the above method are as follows:

(1) Problem and defect in the method for obtaining mineral contents of fine-grained mixed sedimentary rocks. At present, in the method of using thin section observation to count the content of different types of minerals, only local parts of the entire sample can be observed through thin section, and mineral content of the entire sample cannot be accurately characterized, with strong subjectivity in the mineral content estimation process.

(2) There is usually strong heterogeneity in continental fine-grained mixed sedimentary rocks, and the current methods of classifying continental fine-grained mixed sedimentary rocks, in which samples are collected with geological hammers, cannot accurately distinguish different types of fine-grained mixed sedimentary rocks, resulting in large errors in determining the precise location and the exact thickness of different types of fine-grained mixed sedimentary rocks. Moreover, this method cannot effectively remove the diagenetic minerals, and the mixing of diagenetic minerals will lead to errors in the identification of fine-grained mixed sedimentary rock types.

(3) Problem and defect in the expression of sedimentary structures. A sample of fine-grained mixed sedimentary rocks usually contains two or more different lamina, for example, carbonate laminae, clay laminae, silt laminae and the like. Different laminae are characterized by different depositional processes and different reservoir and rock mechanics characteristics, and "laminated" is generally used to describe the sedimentary structure of samples in the prior art, which is difficult to characterize the mixed sedimentation phenomenon of combination of different lamina or laminar couplets.

(4) Total organic carbon (TOC) content is a key parameter for the identification of high-quality fine-grained mixed sedimentary rock types and the evaluation of shale oil and gas resources, and the TOC contents of different types of fine-grained mixed sedimentary rocks have obvious differences. Typically, fine-grained mixed sedimentary rocks with a TOC value of less than 0.5%, represent poor source rocks; those with a TOC value of between 0.5% and 1.0%, represent effective source rocks; those with a TOC value of between 1.0% and 2.0%, represent good source rocks; those with a TOC value of between 2.0% and 4.0%, represent high-quality source rocks; and those with a TOC value of greater than 4.0%, represent extremely high-quality source rocks. In previous technical solutions, this parameter was rarely used to classify fine-grained mixed sedimentary rock types.

The above analysis of the prior art is made by inventors of the present application for the purpose of research and development, and does not necessarily belong to the disclosure of the prior art.

SUMMARY

With respect to problems existing in the prior art, the present disclosure provides a classification method and system for fine-grained mixed sedimentary rocks, a medium, and a terminal. It not only effectively avoids the influence of diagenetic minerals, but also can characterize different types of fine-grained mixed sedimentary rocks more completely and accurately, so as to provide more details in the sequence of fine-grained mixed sedimentary rock types, which has important guiding significance for clarifying the sweet spots of shale oil and gas development.

The present disclosure is implemented by a classification method for fine-grained mixed sedimentary rocks including:

performing detailed description of the cores, and marking and systematic sampling intervals with different sedimentary structures that can be visually identified. Wherein half of each sample is used for a thin section observation, and in the other half thereof, the parts with different sedimentary structures, unidentifiable by the visual examination but observable on the thin section, are further distinguished according to the microscopic observation results of the thin section, and are marked. By using the micro-drilling sampling technique, powder samples are collected from the parts with different sedimentary structures while avoiding diagenetic minerals. Each powder sample are performed a mineral content analysis and a total organic carbon (TOC) content analysis to obtain the contents of different types of minerals and total organic carbon (TOC) contents in the samples. Wherein the different types include a "laminated" type and a fine-grained mixed sedimentary rock type; dividing the "laminated" type into multiple laminar couplets types, to determine the mixed sedimentation characteristics of combination of different lamina or laminar couplets; and, marking the total organic carbon (TOC) content before the name of the fine-grained mixed sedimentary rock type (i.e., the basic rock type+the name of sedimentary structure).

Wherein the powder samples are performed by X-ray diffraction mineral content analysis to obtain the contents of different types of minerals in the samples. In terms of the sedimentary structure expression, the "laminated" is subdivided into the types of laminated carbonate-clay couplets, laminated carbonate-silt couplets, laminated clay-silt couplets, and laminated carbonate-clay-silt triplets (i.e., alternating carbonate laminae, clay laminae, and silt laminae), clearly pointing out the mixed sedimentation phenomenon of combination of different lamina or laminar couplets. The total organic carbon (TOC) content is added at the beginning of the name of the fine-grained mixed sedimentary rock type (i.e., the basic rock type+the name of sedimentary structure).

Further, the classification method for fine-grained mixed sedimentary rocks also includes:
naming the fine-grained mixed sedimentary rocks with a TOC value of less than 0.5% as extremely organic matter-poor, naming that with a TOC value of between 0.5% and 1.0% as organic matter-poor; naming that with a TOC value of between 1.0% and 2.0% as organic matter-bearing, naming that with a TOC value of between 2.0% and 4.0% as organic matter-rich; naming that with a TOC value of greater than 4.0% as extremely organic matter-rich.

Further, the classification method for fine-grained mixed sedimentary rocks also includes:
Step 1: performing a systematic core description, thin section collection and observation to accurately identify the sedimentary structure types of fine-grained mixed sedimentary rock samples and vertical distribution characteristics of the sedimentary structure types through the combination of macroscopic and microscopic analysis, and using micro-drilling to perform a systematic sampling of the fine-grained mixed sedimentary rocks with different types of sedimentary structures while avoiding diagenetic minerals;
Step 2: analyzing the mineral composition and the total organic carbon (TOC) content in each sample by using X-ray diffraction and a high-precision carbon-sulfur analyzer, to obtain the contents of different types of minerals and the total organic carbon (TOC) content in each sample;
Step 3: classifying the basic fine-grained mixed sedimentary rock types by using a triangular classification diagram based on quartz+feldspar contents, carbonate content, and clay minerals contents, to determine 4 major categories and 18 sub-categories of basic rock types are determined.
Step 4: prefixing the names of the classified basic rock types with the names of sedimentary structures, and marking the total organic carbon (TOC) contents of different samples before the names of sedimentary structures.

Further, in the Step 1, by performing the systematic core description, thin section collection and observation, the color, sedimentary structure, biological characteristics, and mineral composition of each fine-grained mixed sedimentary rock sample are described in detail, to emphatically identify the sedimentary structure types of the sample and vertical distribution characteristics of the sedimentary structure types.

Further, in the Step 2, the mineral composition and the total organic carbon (TOC) content in each sample is analyzed by using X-ray diffraction and a high-precision carbon-sulfur analyzer, to obtain the contents of different types of minerals and the total organic carbon (TOC) content in each sample. The sedimentary structures of fine-grained mixed sedimentary rocks include massive structure, laminated structure and middle-thick layered structure (abbreviation for layered structure). Wherein the massive structure is the result of dispersive or uniform mixing of two or three minerals among clay minerals, carbonate and terrigenous clastic minerals, without the feature of lamination. The layered structure refers to a bedding structure formed by alternating different mixed sedimentary rocks or non-mixed sedimentary rocks according to a certain thickness ratio. Single layer of rock vary widely in thickness, ranging from micrometers to meters. A single layer of rock with a thickness of less than 1 cm is defined as the laminated structure, and that with a thickness of larger than 1 cm is defined as the layered structure. The laminated structure includes laminated carbonate-clay couplets, laminated carbonate-silt couplets, laminated clay-silt couplets, and laminated carbonate-clay-silt triplets.

Further, in the Step 3, the triangular classification diagram based on quartz+feldspar content, carbonate content, and clay minerals content is used to classify the basic fine-grained mixed sedimentary rock types. Wherein three end-members of the triangular diagram are respectively: (1) clay minerals end-member A, the sum of clay minerals including kaolinite, illite, and chlorite of clay-grade grain sizes; (2) carbonate end-member C, including various carbonate minerals of chemical and bio-chemical origin, mainly calcite and dolomite; (3) terrigenous clastic mineral end-member S, including quartz and feldspar; wherein in the continental fine-grained mixed sedimentary rocks, the quartz and the feldspar are mainly scattered silt-grade grains, and in addition, the terrigenous clastic grains can also occur in the form of sandstone bands in the fine-grained mixed sedimentary rocks.

The S-A-C triangular classification diagram is used to classify 4 major categories and 18 subcategories of basic rock types, of which the 4 major categories are carbonate major category, clay minerals major category, terrigenous clastic major category, and mixed major category. Wherein the mixed major category belongs to the true mixed sedimentary rocks or narrow mixed sedimentary rocks. The carbonate major category, clay minerals major category, and terrigenous clastic major category are further subdivided into 5 categories according to the content standards of 10%, 25%, 50%, 75% and 90% of quartz+feldspar content, carbonate content, and clay minerals content, respectively, as well as the triangular angular bisectors. The fine-grained mixed sedimentary rocks of mixed sedimentation of carbonate and terrigenous clastic minerals can be classified according to the simplified "binary diagram".

Further, in the Step 4, the names of the classified basic rock types are prefixed by the names of sedimentary structures, including massive structure, layered structure, laminated carbonate-clay couplets, laminated carbonate-silt couplets, laminated clay-silt couplets, and laminated carbonate-clay-silt triplets; and, the total organic carbon (TOC) contents of different samples are marked before the names of sedimentary structures, that is, extremely organic matter-poor, organic matter-poor, organic matter-bearing, organic matter-rich, extremely organic matter-rich.

Another object of the present disclosure is to provide a classification system for fine-grained mixed sedimentary rocks applying the classification method for fine-grained mixed sedimentary rocks, wherein the classification system for fine-grained mixed sedimentary rocks includes:

a sample observation and analysis module, configured to perform a systematical core description, thin section collection and observation, to accurately identify the sedimentary structure types of the fine-grained mixed sedimentary rock samples and vertical distribution characteristics of the sedimentary structure types through the combination of macroscopic and microscopic analysis, and further perform a systematic micro-drilling sampling of the fine-grained mixed sedimentary rocks with different types of sedimentary structures;

a mineral composition and its content determination module, configured to analyze the mineral composition and the total organic carbon (TOC) content of each sample by using X-ray diffraction and a high-precision carbon-sulfur analyzer, to obtain the contents of different types of minerals and the total organic carbon (TOC) content in each sample; and a basic rock type classification module, configured to classify the basic fine-grained mixed sedimentary rock types by using the triangular classification diagram based on quartz+feldspar contents, carbonate content, and clay minerals contents, to determine 4 major categories and 18 sub-categories of basic rock types.

Another object of the present disclosure is to provide a terminal including a memory and a processor, wherein the memory stores computer programs, and when the computer programs are executed by the processor, the processor executes the steps of the classification method for fine-grained mixed sedimentary rocks.

Another object of the present disclosure is to provide a computer-readable storage medium storing computer programs, wherein when the computer programs are executed by the processor, the processor executes the steps of the classification method for fine-grained mixed sedimentary rocks.

The technical solutions to be protected by the present disclosure have the following advantages and positive effects:

First, in view of shortcomings in existing classification methods for continental fine-grained mixed sedimentary rocks, the method has made corresponding improvements.

First of all, in terms of the method for obtaining mineral contents of fine-grained mixed sedimentary rocks, the method is based on detailed core and thin section observations, followed by systematic sampling using micro-drilling sampling technique. After the sample powder was uniformly mixed, X-ray diffraction mineral content analysis is used to obtain the contents of different types of minerals in the samples. This method effectively solves the problem that diagenetic minerals cannot be effectively removed, as well as the subjectivity and one-sidedness problems in the process of estimating mineral contents by thin section observation.

Secondly, in terms of the expression of sedimentary structures, the laminated structure is further subdivided into laminated carbonate-clay couplets, laminated carbonate-silt couplets, laminated clay-silt couplets, and laminated carbonate-clay-silt triplets, which clearly indicates the mixed sedimentation phenomenon of combination of different lamina or laminar couplets.

Finally, the total organic carbon (TOC) content is added at the beginning of the name of the fine-grained mixed sedimentary rock type (i.e., the basic rock type+the name of sedimentary structure). Wherein the fine-grained mixed sedimentary rocks with a TOC value of less than 0.5%, is named as extremely organic matter-poor, that with a TOC value of between 0.5% and 1.0%, is named as organic matter-poor; that with a TOC value of between 1.0% and 2.0%, is named as organic matter-bearing, that with a TOC value of between 2.0% and 4.0%, is named as organic matter-rich; and that with a TOC value of greater than 4.0%, is named as extremely organic matter-rich; which has important significance for clearer and more accurate identification of high-quality fine-grained mixed sedimentary rock types.

Second, the classification method for fine-grained mixed sedimentary rocks provided in the present disclosure complements and improves the type classification and their naming, which has important guiding significance for clarifying the sweet spot of shale oil and gas development. The present disclosure has the advantages of obvious objectivity, accuracy and comprehensiveness over existing technologies at present, with very remarkable progress.

Third, as auxiliary inventiveness evidences of the claims in the present disclosure, the present application also discloses beneficial effects in the following important aspects:

(1) Expected revenue and commercial value achieved by the technical solution transformation of the present disclosure are as follows.

Mainly, the technical solutions serve the shale oil exploration and development of Sinopec Shengli Oilfield, and are also applied to shale oil and gas exploration in regions such as other depressions in the Bohai Bay Basin, and the Jianghan Basin. Because the method successfully reveals the heterogeneous nature of continental oil-bearing shale, it effectively solves the core issue for accurate identification of the sweet spot of shale oil and gas development, not only helping to save shale oil and gas exploration costs and shorten the exploration periods, but also being crucial for drilling horizontal wells and surely facilitating the efficient development and productivity construction of continental shale oil, which is of great significance. The technical solutions of the present disclosure have been highly recognized by Sinopec Shengli Oilfield, Sinopec Jianghan Oilfield, CNOOC Tianjin Branch, etc., and have obtained great economic and social benefits, with wide application prospect and great popularization value.

(2) The technical solutions of the present disclosure solve technical problems that people have been eager to solve without success at all time.

How to correctly classify the fine-grained mixed sedimentary rocks is the core issue for effectively identifying the sweet spot of shale oil and gas development, and is also the key to successful shale oil and gas exploration. Therefore, researchers in oil and gas exploration and development have been eager to establish a classification method for fine-grained mixed sedimentary rocks applicable to theoretical research and production practice, and use the methods to further clarify the high-quality fine-grained mixed sedimentary rock types. The present disclosure establishes such a method. With respect to the problem of strong heterogeneity of fine-grained mixed sedimentary rocks, the method introduces the micro-drilling sampling technique into the systematic sampling work of the present disclosure, which not only effectively solves the problem of the diagenetic minerals cannot being effectively avoided that have plagued researchers in oil and gas exploration and development for a long time, but also allows fine sampling of the fine-grained mixed sedimentary rocks with subtle differences in core and thin section observation. It makes the sequence of the fine-grained mixed sedimentary rock types of single-well cores more detailed and accurate in exploration and development practice.

(3) The technical solutions of the present disclosure overcome technical prejudices.

The present disclosure overcomes the technical prejudices in that the present disclosure provides comprehensive consideration when classifying continental fine-grained mixed sedimentary rocks, establishes the "ternary classification diagram" for fine-grained mixed sedimentary rocks mainly composed of clay minerals, carbonate and terrigenous clastic minerals, and establishes the simplified "binary classification diagram" for fine-grained mixed sedimentary rocks formed by the mixed sedimentation of carbonate and terrigenous clastic minerals, thereby perfecting methods in the art for classifying fine-grained mixed sedimentary rocks only by using "ternary diagram". When naming the fine-grained mixed sedimentary rocks, the present disclosure fully considers their sedimentary structures and total organic carbon contents. Compared with the prior art, it is of great significance for the present disclosure not only to characterize different types of fine-grained mixed sedimentary rocks more accurately, but also to more clearly identify the high-quality fine-grained mixed sedimentary rock types.

BRIEF DESCRIPTION OF DRAWINGS

In order to more clearly illustrate the technical solutions in embodiments of the present disclosure, the accompanying drawings that need to be used in the embodiments of the present disclosure will be briefly introduced below. Obviously, the accompanying drawings described below are only some embodiments of the present disclosure, and those skilled in the art can also obtain other accompanying drawings based on these drawings without creative work done.

FIG. 1 is a flow chart of the classification method for fine-grained mixed sedimentary rocks provided in an embodiment of the present disclosure.

In the drawings:

Figure 2:
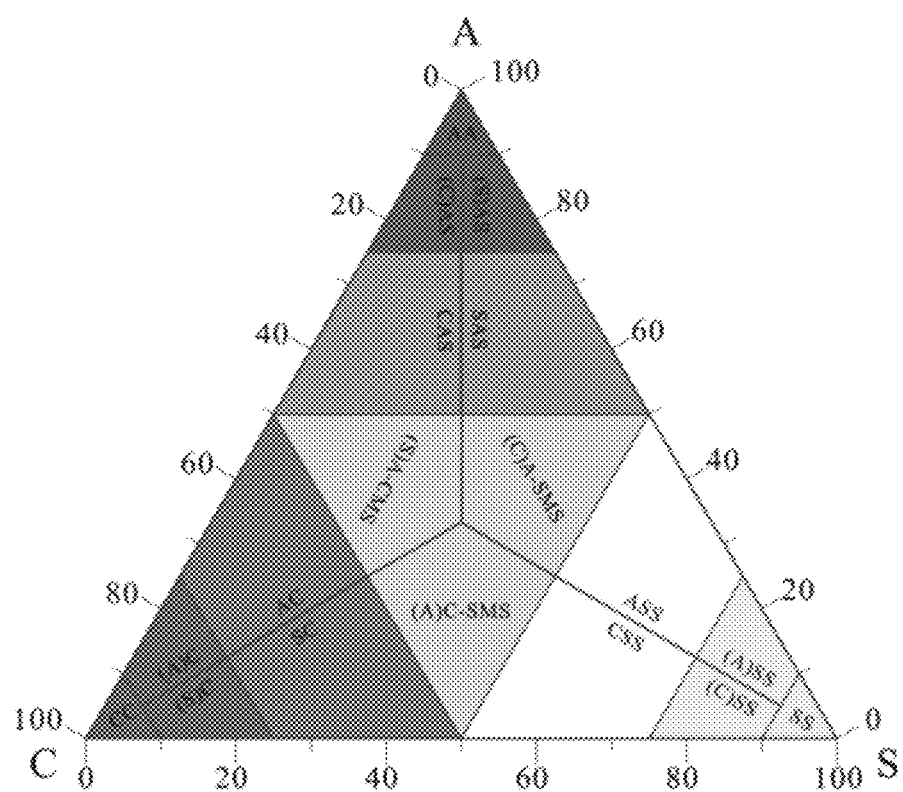
FIG. 2 is a triangular classification diagram based on quartz+feldspar contents, carbonate content, and clay minerals contents for classification of fine-grained mixed sedimentary rocks provided in an embodiment of the present disclosure.

S: sum of terrigenous clastic minerals (quartz+feldspar)
A: sum of clay minerals
C: sum of carbonate minerals (calcite and dolomite)

terrigenous clastic major category: (A)SS represents clay-bearing siliceous fine-grained rock, (C)SS represents carbonate-bearing siliceous fine-grained rock, ASS represents clayey siliceous fine-grained rock, CSS represents calcareous siliceous fine-grained rock, SS represents siliceous fine-grained rock;

carbonate major category: (S)C represents silica-bearing carbonate rock, (A)C represents clay-bearing carbonate rock, SC represents siliceous carbonate rock, AC represents clayey carbonate rock, CC represents carbonate rock;

clay minerals major category: (S)AS represents silica-bearing clayey fine-grained rock, (C)AS represents carbonate-bearing clayey fine-grained rock, SAS represents siliceous clayey fine-grained rock; CAS represents calcareous clayey fine-grained rock; AA represents clayey fine-grained rock;

mixed major category: (C)A-SMS represents carbonate-bearing clayey-siliceous mixed fine-grained rock, (A)C-SMS represents clay-bearing calcareous-siliceous mixed fine-grained rock, (C)S-AMS represents carbonate-bearing siliceous-clayey mixed fine-grained rock.

DETAILED DESCRIPTION OF THE EMBODIMENTS

For the purposes, technical solutions, and advantages of the present disclosure to be clearer, the following will provide a further detailed explanation of the present disclosure in combination with embodiments. It should be understood that the specific embodiments described here are only intended to explain the present disclosure and are not intended to limit it.

Term explanation: continental basin: sedimentary basin formed in continental area; Fine-grained mixed sedimentary rocks: sedimentary rock formed with felsic minerals, carbonate and clay minerals as the main composition minerals, under the joint effect of geological factors (at least 2 types thereof) such as mechanical transportation, biogenic-chemical precipitation, volcanic eruption, and hydrothermal upwelling, which is deposited as a mixture of different mineral types or laminar couplets (a single lamina is about 150 μm) or middle-thick layered couplets, with the grain size of generally less than 62.5 μm.

In terms of obtaining the mineral contents of fine-grained mixed sedimentary rocks, the classification method for fine-grained mixed sedimentary rocks provided in the embodiments of the present disclosure, accurately identify the sedimentary structure types of fine-grained mixed sedimentary rock samples and their vertical distribution characteristics through the combination of macroscopic and microscopic analysis, based on systematic core description, thin section collection and observation, performs a systematic sampling of samples with different types of sedimentary structures by using micro-drilling technology, and obtains the contents of different mineral types in the samples and the total organic carbon (TOC) contents of the samples by using X-ray diffraction mineral content analysis and a high-precision carbon-sulfur analyzer after the uniform mixing of the extracted powder samples. In terms of the expression of sedimentary structures, the method subdivides "laminated" into the types of laminated carbonate-clay couplets, laminated carbonate-silt couplets, laminated clay-silt couplets, and laminated carbonate-clay-silt triplets, clearly pointing out the mixed sedimentation phenomenon of combination of different lamina or laminar couplets. The total organic carbon content TOC is added at the beginning of the name of the fine-grained mixed sedimentary rock type.

As shown in FIG. 1, the classification method for fine-grained mixed sedimentary rocks provided in the embodiments of the present disclosure includes the following steps:

101: performing a systematic core description, thin section collection and observation to accurately identify the sedimentary structure types of fine-grained mixed sedimentary rock samples and their vertical distribution characteristics through the combination of macroscopic and microscopic analysis; and performing a systematic sampling of the fine-grained mixed sedimentary rocks with different types of sedimentary structures while avoiding diagenetic minerals, by using micro-drilling;

S102: analyzing the mineral composition and the total organic carbon content (TOC) in each sample by using X-ray diffraction and a high-precision carbon-sulfur analyzer, to obtain the contents of different mineral types and the total organic carbon (TOC) content in each sample;

S103: by using the fine-grained mixed sedimentary rocks triangular classification diagram based on quartz+feldspar contents, carbonate content, and clay minerals contents, 4 major categories and 18 sub-categories of basic rock types are identified;

S104: prefixing the names of the classified basic rock types with the names of sedimentary structures, and marking the total organic carbon (TOC) contents of different samples before the names of sedimentary structures.

Preferably, the classification method for fine-grained mixed sedimentary rocks provided in the embodiments of the present disclosure specifically includes the following steps.

First, conduct detailed core descriptions, and mark and systematic sampling intervals with different sedimentary structures that can be visually identified. Half of each sample is used for the thin section observation, and in the other half thereof, the parts with different sedimentary structures, unidentifiable by the visual examination but observable on the thin section, are further distinguished according to the microscopic observation results of the thin section, and are marked.

During this process, the color, sedimentary structure, biological characteristics, and mineral composition of each fine-grained mixed sedimentary rock sample are described in detail, to emphatically identify the sedimentary structure types of the sample and their vertical distribution characteristics. The micro-drilling sampling technique is used to systematically collect powder samples of the fine-grained mixed sedimentary rocks with different sedimentary structures while avoiding diagenetic minerals.

On this basis, the X-ray diffraction and the high-precision carbon-sulfur analyzer are used to analyze the mineral composition and its content and the total organic carbon (TOC) content in each powder sample, to obtain the contents of different mineral types and the total organic carbon content in each sample (Note: the sedimentary structures of fine-grained mixed sedimentary rocks include massive structure, laminated structure and middle-thick layered structure (abbreviation for layered structure); wherein the massive structure is the result of dispersive or uniform mixing of two or three minerals among clay minerals, carbonate and terrigenous clastic minerals, without the feature of lamination; and the layered structure refers to a bedding structure formed by alternating different mixed sedimentary rocks or non-mixed sedimentary rocks according to a certain thickness ratio. Individual layer of rock vary widely in thickness, ranging from micrometers to meters. Generally, a single layer of rock with a thickness of less than 1 cm is defined as laminated structure, and that with a thickness of larger than 1 cm is defined as layered structure. The laminated structure generally includes the types such as laminated carbonate-clay couplets, laminated carbonate-silt couplets, laminated clay-silt couplets, and laminated carbonate-clay-silt triplets.

Figure 3:
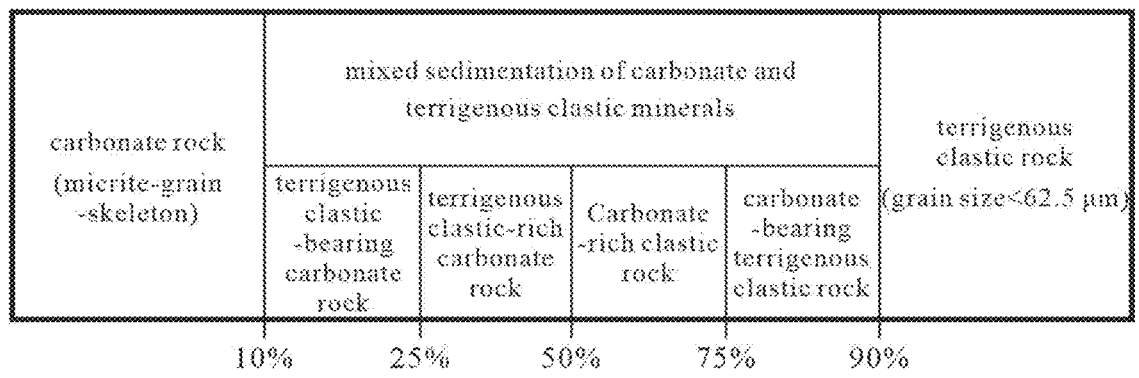
FIG. 3 is a binary classification diagram based on terrigenous clastic and carbonate minerals content for classification of fine-grained mixed sedimentary rocks provided in an embodiment of the present disclosure.

In combination with FIGS. 2 and 3, the triangular classification diagram based on quartz+feldspar content, carbonate content, and clay minerals content is used to classify fine-grained mixed sedimentary rock types, in the embodiments of the present disclosure. The three end-members of the triangular classification diagram in the method are respectively: (1) clay minerals end-member A, the sum of clay minerals such as kaolinite, illite, and chlorite of clay-grade grain sizes; (2) carbonate end-member C, including various carbonate minerals of chemical and bio-chemical origin, mainly calcite and dolomite; wherein in the fine-grained mixed sedimentary rocks, the carbonate are usually of micritic structure, with coarser-grained carbonate minerals occasionally mingled; and (3) terrigenous clastic mineral end-members S, mainly referring to minerals such as quartz and feldspar; wherein in the continental fine-grained mixed sedimentary rocks, the quartz and the feldspar are generally silt-grade grains mingled in a dispersive state, and in addition, the terrigenous clastic grains can also occur in the form of sandstone bands in the fine-grained mixed sedimentary rocks.

The S-A-C triangular classification diagram is used to classify 4 major categories and 18 subcategories of basic rock types, of which the 4 major categories are carbonate major category, clay minerals major category, terrigenous clastic major category, and mixed major category. The mixed major category belongs to the true mixed sedimentary rocks or narrow mixed sedimentary rocks. The carbonate major category, clay minerals major category, and terrigenous clastic major category are further subdivided into 5 categories according to the content standards of 10%, 25%, 50%, 75% and 90% of quartz+feldspar content, carbonate content, and clay minerals content, respectively, as well as the triangular angular bisectors. Such a classification can well distinguish types and trends of mixed sedimentation. The fine-grained mixed sedimentary rocks of mixed sedimentation of carbonate and terrigenous clastic minerals can be classified according to the simplified "binary classification diagram".

The names of the classified fine-grained mixed sedimentary rocks are preceded by their sedimentary structures, that is, massive structure, layered structure, laminated carbonate-clay couplets, laminated carbonate-silt couplets, laminated clay-silt couplets, and laminated carbonate-clay-silt triplets. Finally, the total organic carbon (TOC) content designations (i.e., extremely organic matter-poor, organic matter-poor, organic matter-bearing, organic matter-rich, extremely organic matter-rich) of different samples are placed before their sedimentary structures.

The classification system for fine-grained mixed sedimentary rocks provided in the embodiments of the present disclosure includes:

a sample observation and analysis module, configured to perform the systematic core description, thin section collection and observation, to accurately identify the sedimentary structure types of the fine-grained mixed sedimentary rock samples and their vertical distribution characteristics through the combination of macroscopic and microscopic analysis, and perform a systematic micro-drilling sampling of the mixed sedimentary rocks with different types of sedimentary structures;

a mineral composition and its content determination module, configured to analyze the mineral composition and the total organic carbon (TOC) content of each sample by using X-ray diffraction and a high-precision carbon-sulfur analyzer, to obtain the contents of different types of minerals and the total organic carbon (TOC) content in each sample; and a basic rock type classification module, configured to classify the fine-grained mixed sedimentary rock types by using the triangular classification diagram based on quartz+feldspar contents, carbonate content, and clay minerals contents, to determine 4 major categories and 18 sub-categories of basic rock types.

Evidence for relevant effects of the embodiments. The embodiments of the present disclosure have achieved some positive effects in the process of research and development or use, and indeed have significant advantages over the prior art, which will be described below in combination with the data, charts and the like in the experimental process.

In the embodiments of the present disclosure, the continuous fine-grained mixed sedimentary rocks of wells NY1, FY1, and LY1 in the Dongying Depression and Well Luo69 in the Zhanhua Depression, of the Bohai Bay Basin, are selected as the implementation objects of the classification of fine-grained mixed sedimentary rocks. Firstly, the systematic core description, thin section collection and observation are performed for wells NY1, FY1, LY1, and Luo69 (in the embodiments of the present disclosure, a Leica DM2500 microscope from Germany is used to conduct observation and description of the thin sections), to describe in detail the macroscopic and microscopic rock textures, sedimentary structures, distribution characteristics of carbonate minerals, and fossils and the like of the fine-grained mixed sedimentary rocks, thereby accurately distinguishing and marking the parts with different sedimentary structures, and carefully identifying the possible diagenetic minerals (such as sparry calcite veins and pyrite bands) present in the fine-grained mixed sedimentary rocks in combination with cathodoluminescence (in the embodiments of the present disclosure, a CITL CL8200 MKS cathodoluminescence instrument from UK mounted on a Leica DM2500 microscope from Germany is used to carry out the research). Based on the thin section observations, the parts affected by obvious diagenesis are excluded, and then micro-drilling technique was used to systematically collect powder samples from the parts with different sedimentary structures in the areas that were not affected by obvious diagenesis, by using the micro-drilling technology (a NEW WAVE Micro-Mill microsampling instrument from the United States is used in the embodiments of the present disclosure). After the completion of the sampling, an X-ray diffraction mineral content analysis (a Panalytical X'Pert PRO DY2198 X-ray diffractometer from the Netherlands is used in the embodiments of the present disclosure) and a total organic carbon content (TOC) analysis (an LECO CS600 high-precision carbon-sulfur analyzer from the United States is used in the embodiments of the present disclosure) are performed on the drilled sample powders, to determine the contents of different mineral types and the total organic carbon (TOC) contents in the samples from different sedimentary structures.

The contents of different mineral types obtained from the X-ray diffraction mineral content analysis of each sample are combined by the rule: the sum of quartz and feldspar contents as the terrigenous clastic mineral sum (S), clay minerals content as the clay minerals sum (A), the sum of calcite and dolomite contents as the carbonate sum (C). Total terrigenous clastic minerals (S), total clay minerals (A), and total carbonate (C) are calculated for all samples and then plot them on the ternary classification diagram and binary classification diagram for classification of fine-grained mixed sedimentary rocks. It should be noted that the binary diagram is only limited to the fine-grained mixed sedimentary rocks formed by the mixed sedimentation of terrigenous clastic and carbonate minerals.

The samples plot on different type zones of the ternary classification diagram and binary classification diagram for classification of fine-grained mixed sedimentary rocks are named separately, and the basic principles of naming are shown in FIGS. 2 and 3, respectively. All named fine-grained mixed sedimentary rock samples are preceded by their respective sedimentary structures, including massive structure, layered structure, laminated carbonate-clay couplets, laminated carbonate-silt couplets, laminated clay-silt couplets, and laminated carbonate-clay-silt triplets; further, the designation represented by the TOC content of each sample is added before the sedimentary structures (with the TOC value of the sample less than the designation is named as extremely organic matter-poor; with the TOC value of the sample between 0.5% and 1.0%, named as organic matter-poor; with the TOC value of the sample between 1.0% and 2.0%, named as organic matter-bearing; with the TOC value of the sample between 2.0% and 4.0%, named as organic matter-rich; with the TOC value of the sample greater than 4.0%, named as extremely organic matter-rich); thereby completing the type classification and naming of the fine-grained mixed sedimentary rock samples. This has important guiding significance for clarifying the sweet spots of shale oil and gas development. Compared with the current existing technologies, the present disclosure has obvious objectivity in the mineral content analysis, obvious accuracy in the identification of the types of fine-grained mixed sedimentary rocks, and obvious comprehensiveness in the naming of fine-grained mixed sedimentary rocks; which has important guiding significance for cost-saving and efficiency-improving in shale oil and gas exploration, with remarkable progress.

It should be noted that the embodiments of the present disclosure can be realized by hardware, software, or a combination thereof. The hardware part can be implemented by using dedicated logic; the software part can be stored in memory and executed by a suitable instruction execution system such as microprocessors or specialized design hardware. Those skilled in the art can understand that the above terminals and method can be implemented by using computer-executable instructions and/or control codes contained in processors, and for example, such codes are provided in carrier media such as disks, CDs, or DVD-ROMs, programmable memories such as read-only memories (firmware), or data carriers such as optical or electronic signal carriers. The system and its modules of the present disclosure can be implemented by such as Very Large Scale Integration (VLSI) or gate arrays, semiconductors such as logic chips and transistors, or hardware circuits of programmable hardware devices such as field programmable gate arrays and programmable logic devices; and can also be implemented by software executed by various types of processors, or by a combination of the above-mentioned hardware circuits and software, such as firmware.

What is described above is only specific embodiments of the present disclosure, but the protection scope of the present disclosure is not limited thereto. Any modifications, equivalent replacements, improvements and the like within the spirit and principle of the present disclosure, made within the technical scope disclosed in the present disclosure by those familiar with the art, shall fall within the protection scope of the present disclosure.

What is claimed is:

1. A classification method for fine-grained mixed sedimentary rocks, comprising:
performing a core description, thin section collection and observation;
performing a mineral content analysis and a total organic carbon content analysis after micro-drilling sampling and mixing samples evenly, to obtain content values of different types of minerals and total organic carbon contents in the samples;
the different types comprising a laminated type and a fine-grained mixed sedimentary rock type;
dividing the laminated type into multiple laminar couplets types, to determine a mixed sedimentation of combination of different lamina or laminar couplets;
marking the total organic carbon content before the name of the fine-grained mixed sedimentary rock type; and
performing a systematic sampling of the fine-grained mixed sedimentary rocks with different types of sedimentary structures while avoiding diagenetic minerals via the core description and the thin section collection and observation, in the micro-drilling sampling.

2. The classification method for fine-grained mixed sedimentary rocks according to claim 1, wherein the step of dividing the laminated type into multiple laminar couplets types, comprises:
laminated carbonate-clay couplets, laminated carbonate-silt couplets, laminated clay-silt couplets, and laminated carbonate-clay-silt triplets.

3. The classification method for fine-grained mixed sedimentary rocks according to claim 1, wherein the core description, thin section collection and observation, comprises:
accurately identifying sedimentary structure types of the fine-grained mixed sedimentary rock samples and vertical distribution characteristics of the sedimentary structure types with the combination of macroscopic and microscopic views; comprehensively analyzing the color, sedimentary structures, biological characteristics, mineral composition in each fine-grained mixed sedimentary rock sample from the macroscopic and microscopic perspectives, to accurately identify the sedimentary structure types of the samples and vertical distribution characteristics of the sedimentary structure types, as well as the characteristics and distribution of diagenetic minerals in the samples.

4. The classification method for fine-grained mixed sedimentary rocks according to claim 1, wherein the step of performing a mineral content analysis and a total organic carbon content analysis, to obtain content values of different types of minerals and total organic carbon contents comprises:
performing the mineral composition analysis and the total organic carbon content analysis of each sample by using an X-ray diffractometer, to obtain contents of different minerals and the total organic carbon content in each sample; and
the fine-grained mixed sedimentary rocks comprising massive structure, laminated structure and layered structure; wherein the massive structure is the result of dispersive or even mixing of two or three of clay minerals, carbonate minerals and terrigenous clastic minerals; the layered structure is a bedding structure formed by mixing different mixed sedimentary rocks or nonmixed sedimentary rocks; a single rock bed with a thickness of less than 1 cm is defined as the laminated structure, and a single rock bed with a thickness of greater than 1 cm is defined as the layered structure; and, the laminated structure includes laminated carbonate-clay couplets, laminated carbonate-silt couplets, laminated clay-silt couplets, and laminated carbonate-clay-silt triplets.

5. The classification method for fine-grained mixed sedimentary rocks according to claim 1, wherein, a fine-grained mixed sedimentary rocks triangular diagram classification method based on mineral contents is used to classify the fine-grained mixed sedimentary rock types;
wherein three end-members of the triangular classification diagram are respectively:
(1) clay minerals end-member A, the sum of clay minerals comprising kaolinite, illite, and chlorite of clay-grade grain sizes;
(2) carbonate end-member C, comprising various carbonate minerals of chemical and biochemical origin; wherein in the fine-grained mixed sedimentary rocks, the carbonate minerals are of micritic structure, with coarser granular carbonate minerals occasionally mingled;
(3) terrigenous clastic mineral end-member S, minerals comprising quartz and feldspar; wherein in continental fine-grained mixed sedimentary rocks, the quartz and the feldspar are siltgrade grains mingled in a dispersive state, and the terrigenous clastic grains are mingled into the fine-grained mixed sedimentary rocks in a form of sandstone bands;
wherein the triangular classification diagram is used to classify 4 major categories and 18 subcategories of rock types, the 4 major categories of which are respectively carbonate, clay, sand and mixed major categories;
wherein the mixed major category belongs to the true mixed sedimentary rocks or narrow mixed sedimentary rocks; and
wherein the carbonate, clay, and sand major categories are further respectively subdivided into 5 categories according to content standards of 10%, 25%, 50%, 75% and 90% and triangular angular bisectors.

6. The classification method for fine-grained mixed sedimentary rocks according to claim 1, wherein the step of marking the total organic carbon content before the name of the fine-grained mixed sedimentary rock type comprises:
prefixing the classified basic rock types with the names of sedimentary structures, comprising the massive structure, layered structure, laminated carbonate-clay couplets, laminated carbonate-silt couplets, laminated clay-silt couplets, and laminated carbonate-clay-silt triplets; and
marking the total organic carbon contents of different samples before the sedimentary structures, that is, extremely organic matter-poor, organic matter-poor, organic matter-bearing, organic matter-rich, extremely organic matter-rich.

7. A system for applying the classification method for fine-grained mixed sedimentary rocks according to claim 1, comprising:
a sample observation and analysis module, configured to perform the core description, thin section collection and observation, to accurately identify the sedimentary structure types of the fine-grained mixed sedimentary rock samples and vertical distribution characteristics of the sedimentary structure types with the combination of macroscopic and microscopic views, and perform a systematic micro-drilling sampling of the mixed sedimentary rocks with different sedimentary structures;

a mineral composition and its content determination module, configured to analyze the mineral composition and the total organic carbon content in each sample by an X-ray diffractometer, to obtain the contents of different minerals in each sample; and a rock type classification module, configured to classify the fine-grained mixed sedimentary rock types by using the triangular classification diagram based on mineral contents.

8. A terminal, comprising a memory and a processor, wherein the memory stores computer programs, and when the computer programs are executed by the processor, the processor executes the steps of the classification method for fine-grained mixed sedimentary rocks according to claim 1.

9. A non-transitory computer-readable storage medium storing computer programs, wherein when the computer programs are executed by the processor, the processor executes the steps of the classification method for fine-grained mixed sedimentary rocks according to claim 1.

\* \* \* \* \*